United States Patent [19]

Topholm

[11] Patent Number: 4,706,778

[45] Date of Patent: Nov. 17, 1987

[54] IN-THE-EAR-CANAL HEARING AID

[75] Inventor: Jan Topholm, Värløse, Denmark

[73] Assignee: Topholm & Westermann ApS, Värløse, Denmark

[21] Appl. No.: 920,550

[22] Filed: Oct. 20, 1986

[30] Foreign Application Priority Data

Nov. 15, 1985 [DE] Fed. Rep. of Germany ....... 3540579

[51] Int. Cl.[4] ................................................ A61B 7/02

[52] U.S. Cl. .................................... 181/135; 381/68.6

[58] Field of Search ................ 181/135, 130; 381/68.6

[56] References Cited

U.S. PATENT DOCUMENTS 4,010,820 3/1977 Johnson ............................ 181/135

4,311,206 1/1982 Johnson ............................ 181/135

*Primary Examiner*—Benjamin R. Fuller

*Attorney, Agent, or Firm*—Sughrue, Mion, Zinn, Macpeak, and Seas

[57] ABSTRACT

The invention relates to an in-the-ear hearing aid for people with impaired or defective hearing, with an ear-piece containing a microphone, amplifier, telephone, battery compartment with battery, on/off switch and volume control and closed by a cover plate; a hollow space (6) to the auricular canal is provided for at the inner end of the ear-piece (1) between the sound outlet connector (4) of the telephone (3) and the sound outlet (5) of the hearing air, this hollow space forming a resonator in conjunction with the sound outlet.

5 Claims, 5 Drawing Figures

Figure 5:
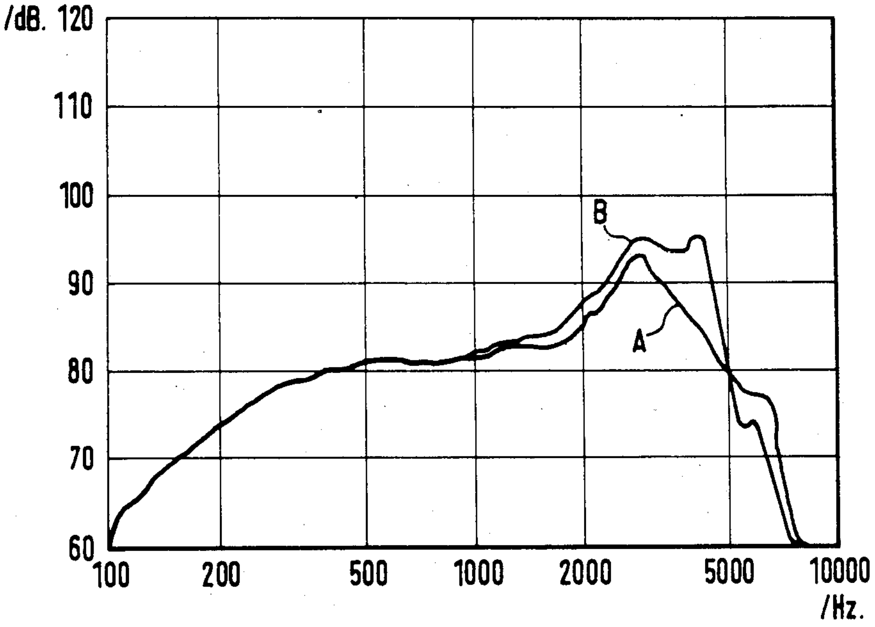

Fig. 1
PRIOR ART
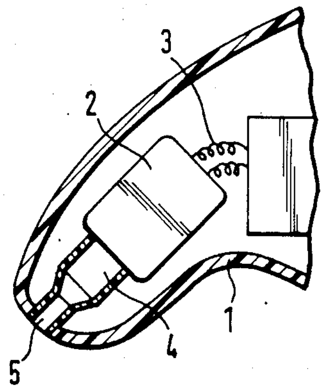
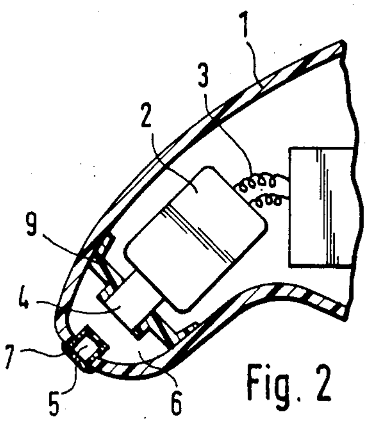
Fig. 2
Fig. 3
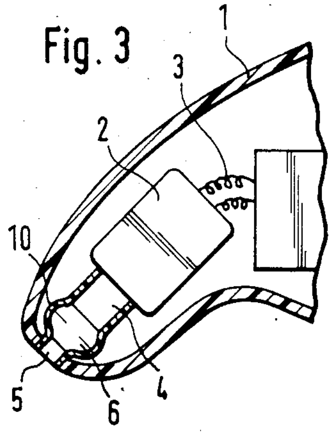
Fig. 4
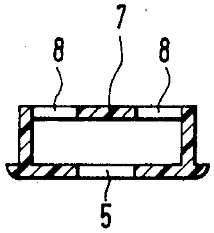

IN-THE-EAR-CANAL HEARING AID

The invention relates to an in-the-ear-canal hearing aid for people with impaired or defective hearing, with an ear-piece containing a microphone, amplifier, telephone, battery compartment with battery, on/off switch and volume control and closed by a cover plate.

Many types of such hearing aids are generally known. In this type of hearing aid, the telephone is normally connected to the hearing aid outlet by means of an extremely short, thin pipe or a corresponding short, thin tube. The reason for this is an attempt to place the telephone as deeply as possible in the ear or auricular canal due to the extremely limited space available. Unfortunately, in the case of currently available telephones, this has resulted in a frequency response with a particularly marked resonance peak at high frequencies, this being highly undesirable.

In addition, there is a risk of cerumen penetrating into these small pipes, first blocking them and then penetrating into the sound outlet connector of the telephone, making the latter permanently unuseable.

The invention aims to avoid the disadvantages of this known arrangement, and in particular to improve the frequency response of the sound emitted to the ear.

The invention achieves this by providing for a resonance chamber towards the auricular canal at the inner end of the ear-piece between the sound outlet connector of the telephone and the sound outlet of the hearing aid.

The best solution is obtained by fitting a replaceable cerumen collector with one or several bores at the sound outlet of the hearing aid.

Other design features of the invention can be found in the other claims.

The invention will now be explained in more detail, taking various embodiments in conjunction with the enclosed figures.

The figures show:

FIG. 1 a partial section of a hearing aid in accordance with the current state of the art;

FIG. 2 a partial section of an in-the-ear-hearing aid in accordance with the invention;

FIG. 3 a partial section of the further embodiment of the invention;

FIG. 4 a particularly favorable cerumen collector design and

FIG. 5 a diagram to show the frequency response of hearing aids in accordance with the latest state of the art and in accordance with the invention in respect of the sound emitted to the ear.

FIG. 1 shows a cross-sectional view of the bottom section of an in-the-ear hearing aid in accordance with the latest state of the art. An ear-piece 1 contains a telephone at its bottom end, this being connected by conductors 3 to the other sections of the hearing aid. These are not shown since they do not form part of the invention. The sound outlet connector 4 of the telephone is routed outwards through a small pipe, this forming the sound outlet 5 of the hearing aid.

The disadvantages of this arrangement have already been explained above.

In FIG. 2, one can see that a resonance chamber 6 is provided between the sound outlet connector 4 of the telephone 2 and the sound outlet of the hearing aid 5. In addition, a replaceable cerumen collector 7 can be seen at the bottom end of the ear-piece.

This resonance chamber is an acoustic resonator. It is possible to achieve a smooth frequency response with wide emphasis at higher frequencies by appropriately dimensioning the volume of the resonance chamber 6 and the diameter of the bore leading to the auricular canal or the bores leading to the auricular canal. This is desirable not just to compensate for the loss of resonance in the auricular canal when a hearing aid is inserted, but also to compensate for the most common types of hearing loss.

If the cerumen collector 7 is replaceable, this enables it to be taken out easily and cleaned or replaced when blocked. If cerumen should penetrate this replaceable part, it will initially be deposited in the resonance chamber, thus neither preventing sound emission nor making the telephone unuseable.

It is also possible to see a collar 9 supporting the telephone 2, the collar being penetrated by the sound outlet connector 4 of the telephone. This collar, consisting of a sift plastic material, may also be used in determining the resonance of the resonance chamber in respect of volume.

FIG. 3 shows a further embodiment of the invention. The same parts are provided with the same reference numbers and are not mentioned again. In this case, the telephone 2 is connected to the sound outlet 5 of the hearing aid at the telephone's sound outlet connector 4 by means of a sound outlet duct 10 and is extended to form a resonance chamber 6 between these two channels. It is easy to see that different volumes of the resonance chamber 6 may be obtained by varying the shape of the sound outlet duct 10.

FIG. 4 shows a possible design for a cerumen collector 7. Two bores 8 lead to the common sound outlet 5 of the hearing aid.

Generally, it is conceiveable that two or more parallel bores 8 be provided instead of a continuous bore as shown in FIG. 2. The volume of the resonance chamber and the volume of the bores must always be taken into consideration to achieve the desirable compensation and smoothing of frequency response with wide emphasis at higher frequencies.

FIG. 5 shows the frequency responses which were measured on a state-of-the-art hearing aid and on a hearing aid in accordance with the invention. Curve A follows the same path as curve B to approximately 1.6 kHz. In the case of the state-of-the-art hearing aid, there is a marked peak at approximately 3 kHz followed by a sharp drop.

Curve B, measured for the hearing aid designed in accordance with the invention, increases more steeply above approximately 1 kHz and has a wide peak where there is approximately equal amplification between 2.5 and 4.5 kHz. The curve then falls more steeply above 4.5 kHz, as might be expected, meeting curve A at 5 kHz, but then falling even more steeply to 60 dB at approximately 7 kHz.

It is therefore clear that wide emphasis at higher frequencies is possible with this new kind of resonance chamber.

I claim:

1. In-the-ear-canal hearing aid for people with impaired or defective hearing comprising: an ear-piece (1) containing a microphone, amplifier, telephone, battery compartment with battery, on/off switch and volume control and closed by a cover plate, the improvement wherein a hollow space (6) is formed at the inner end of the ear-piece between the sound outlet connector (4) of the telephone (3) and the sound outlet (5) of the hearing aid to the auricular canal, forming a resonator in conjunction with the sound outlet, and wherein a replaceable cerumen collector (7) with at least one bore (8) is fitted at the sound outlet (5) of the hearing aid, forming an integrated part of the resonator, which can be tuned by changing the dimensions of the at least one bore in the cerumen collector.

2. Hearing aid in accordance with claim 1, characterized by the fact that the resonance chamber (6) is closed off by a collar (9) which touches the inner wall of the ear-piece on all sides, supports the telephone and is penetrated by the sound outlet connector (4) of the telephone (3).

3. Hearing aid in accordance with claim 1, wherein a bellied sound outlet duct constitutes said hollow space acting as a resonator (6) between the sound outlet connector of the telephone (3) and the sound outlet of the hearing aid.

4. Hearing aid in accordance with claims 1 and 2, wherein the cerumen collector (7) has several bores (8) leading from the outside to the inside.

5. Hearing aid in accordance with claim 4, wherein several bores (8) join together to form a common duct, constituting the sound (5) outlet of the hearing aid.

* * * * *